(12) United States Patent
Shuman

(10) Patent No.: US 11,844,561 B2
(45) Date of Patent: Dec. 19, 2023

(54) CURRENT INRUSH REGULATOR

(71) Applicant: GYRUS ACMI, INC., Westborough, MA (US)

(72) Inventor: Brandon J. Shuman, Redmond, WA (US)

(73) Assignee: Gyrus ACMI, Inc., Westborough, MA (US)

( * ) Notice: Subject to any disclaimer, the term of this patent is extended or adjusted under 35 U.S.C. 154(b) by 956 days.

(21) Appl. No.: 16/477,708

(22) PCT Filed: Jan. 17, 2017

(86) PCT No.: PCT/US2017/013812
§ 371 (c)(1),
(2) Date: Jul. 12, 2019

(87) PCT Pub. No.: WO2018/136039
PCT Pub. Date: Jul. 26, 2018

(65) Prior Publication Data
US 2019/0357961 A1 Nov. 28, 2019

(51) Int. Cl.
*A61B 18/12* (2006.01)
*A61B 1/267* (2006.01)
(Continued)

(52) U.S. Cl.
CPC ........ *A61B 18/1233* (2013.01); *A61B 1/2676* (2013.01); *A61B 18/1482* (2013.01);
(Continued)

(58) Field of Classification Search
CPC ............ A61B 18/1233; A61B 18/1482; A61B 1/2676; A61B 90/04; A61B 2017/0034;
(Continued)

(56) References Cited

U.S. PATENT DOCUMENTS 5,581,192 A * 12/1996 Shea ...................... H01H 29/06
324/555
5,633,578 A * 5/1997 Eggers ............... A61B 18/1206
323/911
(Continued)

FOREIGN PATENT DOCUMENTS

| WO | WO-2011006009 A1 * | 1/2011 | ............. A61B 17/54 |
| WO | WO-2015192027 A1 | 12/2015 | |
| WO | WO-2018136039 A1 | 7/2018 | |

OTHER PUBLICATIONS

"International Application Serial No. PCT/US2017/013812, International Preliminary Report on Patentability dated Aug. 1, 2019", 8 pgs.

(Continued)

*Primary Examiner* — Khadijeh A Vahdat
*Assistant Examiner* — Abigail M Ziegler
(74) *Attorney, Agent, or Firm* — Schwegman Lundberg & Woessner, P.A.

(57) ABSTRACT

Disclosed embodiments include an apparatus, a system and a method for shunting current between first and second electrodes to temporarily reduce current applied through first and second electrodes. In a nonlimiting embodiment, an illustrative apparatus includes first and second electrode couplings configured to electrically engage proximal ends of the first and second electrodes, respectively, the first and second electrodes each having a distal end configured to conduct electrical current generated by a switchable current source therebetween and through an electrically conductive target. A current inrush regulator is configured to temporarily shunt at least a portion of the electrical current generated by the switchable current source to temporarily reduce the (Continued)

electrical current passing between the distal ends of the first and second electrodes through the electrically conductive target.

13 Claims, 9 Drawing Sheets

(51) Int. Cl.
    *A61B 18/14*         (2006.01)
    *A61B 90/00*         (2016.01)
    *A61B 17/00*         (2006.01)
    *A61B 18/00*         (2006.01)

(52) U.S. Cl.
    CPC ....... *A61B 90/04* (2016.02); *A61B 2017/0034* (2013.01); *A61B 2018/0072* (2013.01); *A61B 2018/00083* (2013.01); *A61B 2018/00541* (2013.01); *A61B 2018/1472* (2013.01); *A61B 2218/007* (2013.01)

(58) Field of Classification Search
    CPC ........... A61B 2018/00083; A61B 2018/00541; A61B 2018/0072; A61B 2018/1472; A61B 2018/00577; A61B 2018/00791; A61B 2018/00916; A61B 2218/007
    See application file for complete search history.

(56) References Cited

U.S. PATENT DOCUMENTS

| | | | |
|---|---|---|---|
| 7,371,233 B2 | 5/2008 | Swanson et al. | |
| 2004/0030330 A1 | 2/2004 | Brassell et al. | |
| 2004/0116919 A1* | 6/2004 | Heim | A61B 18/1206 606/34 |
| 2007/0049915 A1* | 3/2007 | Haemmerich | A61B 18/1492 606/41 |
| 2009/0296298 A1* | 12/2009 | Divan | H02H 9/001 361/58 |
| 2010/0201475 A1* | 8/2010 | Kowalik | H01H 87/00 337/21 |
| 2016/0166312 A1* | 6/2016 | Johnston | A61B 18/1206 606/34 |
| 2016/0278840 A1* | 9/2016 | Kane | A61B 18/1482 |
| 2017/0189101 A1* | 7/2017 | Yates | A61B 18/1445 |
| 2019/0066953 A1* | 2/2019 | Furuuchi | H01H 87/00 |

OTHER PUBLICATIONS

"International Application Serial No. PCT/US2017/013812, International Search Report dated Oct. 19, 2017", 5 pgs.
"International Application Serial No. PCT/US2017/013812, Written Opinion dated Oct. 19, 2017", 6 pgs.

\* cited by examiner

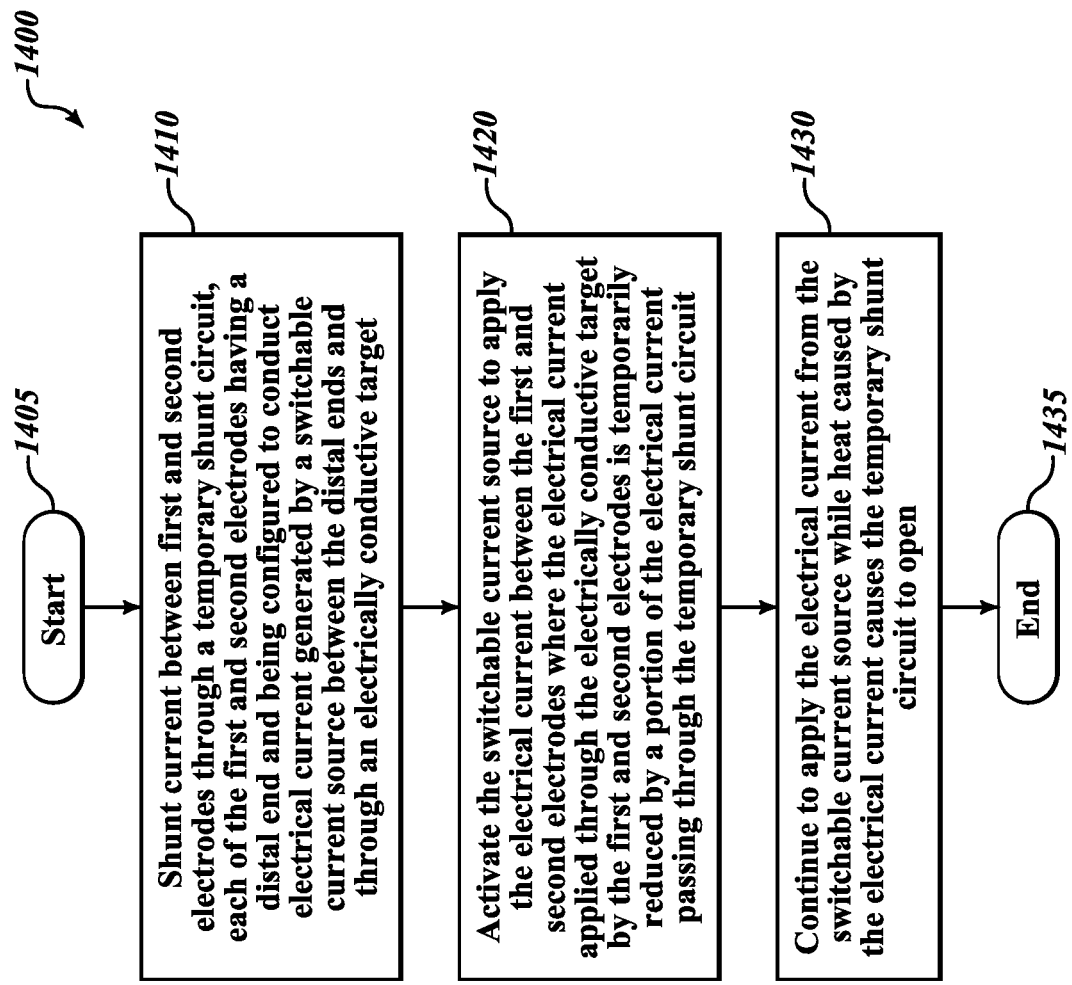

CURRENT INRUSH REGULATOR

FIELD

The present disclosure relates to temporarily reducing an electrical current applied to an electrically conductive target between two electrodes.

BACKGROUND

The statements in this section merely provide background information related to the present disclosure and may not constitute prior art.

Electrical current may be applied to a living body or another object in a number of applications. For example, spot welding involves applying current to join two pieces of metal by melting them together. The surge of current through the metal generates heat as a result of resistance of the metal to the surge of current, thereby causing the metal to melt together. However, while the heat generated by the surge of current is desirable in welding, it may be less desirable in other applications.

For example, an electrosurgical instrument used for treating tissue in a living body may selectively apply a surge of current through the tissue. An applicator generally includes one or more electrodes at the distal end. Such electrodes may emit a radio frequency ("RF") electric current to surrounding tissue to coagulate and/or ablate the tissue. Monopolar electrosurgical instruments entail use of one electrode that interacts with a neutral electrode which is connected to the body of a patient. A bipolar electrosurgical instrument typically includes an applicator with two electrodes (that is, a distal electrode and a proximal electrode). An RF voltage with different potentials is applied to such bipolar instruments so that an electrical current passes from one electrode to the other electrode through the tissue, thereby heating the tissue to coagulate and/or ablate the tissue.

However, a sudden surge of current may abruptly generate a quantity of heat through the tissue that may have undesirable effects. A surgeon performing an electrosurgical procedure could manually adjust a current source gradually to try to avoid a sudden surge of current being applied. However, if the treatment involves a very brief application of current, then manually increasing the electrical current level may be impractical.

SUMMARY

Disclosed embodiments include an apparatus coupling a current inrush regulator between electrodes, a system including a current inrush regulator for treating tissue at an electrically conductive target, and a method for applying current through an electrically conductive target using a current inrush regulator.

In an illustrative embodiment, an apparatus includes first and second electrode couplings configured to engage proximal ends of first and second electrodes, respectively, with the first and second electrodes each having a distal end configured to conduct electrical current generated by a switchable current source therebetween and through an electrically conductive target. A current inrush regulator is configured to temporarily shunt at least a portion of the electrical current generated by the switchable current source to temporarily reduce the electrical current passing between the distal ends of the first and second electrodes through the electrically conductive target.

In another illustrative embodiment, a system for treating tissue at an electrically conductive target includes a switchable current source configured to selectively provide electrical power between a first pole and a second pole. A bronchoscope is configured to be inserted into a body to convey, toward a vicinity of an electrically conductive target, a sheath containing a primary electrode electrically coupleable to the first pole and a secondary electrode electrically coupleable to the second pole. A positioning handle is configured to position distal ends of the primary electrode and the secondary electrode relative to the electrically conductive target. An electrical conductor is configured to electrically connect the primary electrode to the first pole of the controllable electrical power source and to connect the secondary electrode to the second pole of the electrical power source. A current inrush regulator is electrically coupleable to proximal ends of the primary electrode and the secondary electrode and configured to temporarily shunt at least a portion of the electrical current generated by the switchable current source to temporarily reduce the electrical current passing between the distal ends of the primary and secondary electrodes through the electrically conductive target.

In another illustrative embodiment, a method includes shunting current between first and second electrodes through a temporary shunt circuit, each of the first and second electrodes having a distal end and being configured to conduct electrical current generated by a switchable current source between the distal ends and through an electrically conductive target. The switchable current source is activated to apply the electrical current between the first and second electrodes, where a portion of the electrical current applied through the electrically conductive target by the first and second electrodes is reduced by a portion of the electrical current passing through the temporary shunt circuit. The electrical current is continued to be applied from the switchable current source while heat caused by the electrical current flowing through the temporary shunt circuit causes the temporary shunt circuit to open. A level of the electrical current flowing through the distal ends of the first and second electrodes and the electrically conductive target is reduced until the temporary shunt circuit opens.

Further features, advantages, and areas of applicability will become apparent from the description provided herein. It should be understood that the description and specific examples are intended for purposes of illustration only and are not intended to limit the scope of the present disclosure.

DRAWINGS

The drawings described herein are for illustration purposes only and are not intended to limit the scope of the present disclosure in any way. The components in the figures are not necessarily to scale, with emphasis instead being placed upon illustrating the principles of the disclosed embodiments. In the drawings:

FIG. 14 is a flow diagram of an illustrative method of using a current inrush regulator

DETAILED DESCRIPTION

The following description is merely exemplary in nature and is not intended to limit the present disclosure, application, or uses.

Figure 1:
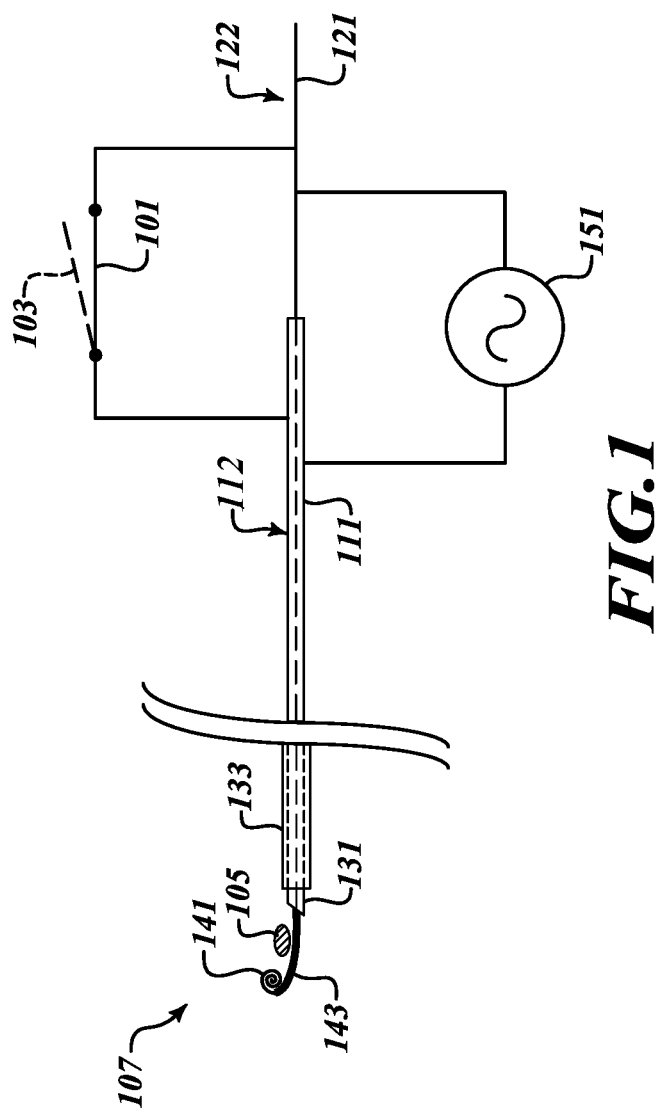
FIG. 1 is a schematic view of an illustrative current inrush regulator.

Given by way of overview and referring to FIG. 1, in an illustrative, non-limiting embodiment a current inrush regulator 101 is provided for temporarily reducing a flow of electrical current through an electrically conductive target 105 within a body 107. The current inrush regulator 101 is configured to present an electrically closed switch to temporarily shunt current across the switch. Heating caused by the flow of electrical current causes the current inrush regulator 101 to transition to an open position 103, thereby removing the temporary shunt circuit. The current inrush regulator 101 thus temporarily diverts a flow of electrical current, as further described below.

The current inrush regulator 101 is electrically coupled to a proximal end 111 of a primary electrode 112 and a proximal end 121 of a secondary electrode 122. Within the body 107, a distal end 131 of the primary electrode 111 is positioned at one side of the electrically conductive target 105 and a distal end 141 of the secondary electrode 122 is positioned at an opposite side of the electrically conductive target 105. The secondary electrode 141 is encased in an insulating sleeve 143 between the distal end 141 of the secondary electrode 122 and the proximal end 121 of the secondary electrode 122. In one embodiment, the distal end 143 of the secondary electrode 122 is extended through the distal end 131 of the primary electrode 112. Both the distal end 131 of the primary electrode 112 and the distal end 141 of the secondary electrode 122 are presented into the body 107 using a sheath 133, which is further described with reference to FIG. 2. It also will be appreciated that the proximal end 111 of the primary electrode 112, another portion of the primary electrode 112, or the distal end 141 of the secondary electrode 122 may be positioned within the electrically conductive target 105 when an electrical current is applied between the primary electrode 112 and the secondary electrode 122, as is further described below.

The proximal end 111 of the primary electrode 112 and the proximal end 121 of the secondary electrode 122 are coupled to a switchable current source 151. Once the distal end 131 of the primary electrode 112 and the distal end 141 of the secondary electrode 112 are situated near the electrically conductive target 105, the switchable current source 151 may be activated. Without the current inrush regulator 101 a surge of current between the distal end 131 of the primary electrode 112 and the distal end 141 of the secondary electrode 122 may cause an undesirable degree of instantaneous heating in the body 107 at or near the electrically conductive target 105. In some cases, it may be desired to apply current-induced heating at the electrically conductive target 105 for a brief interval. In some such cases, reducing an amount of current initially applied in the initial surge may help allow for enhanced control of the degree of heating applied at or near the electrically conductive target 105.

Embodiments of the current inrush regulator 101 temporarily shunt electrical current applied by the switchable current source 151. Temporarily shunting the electrical current applied at least partially diverts a flow of electrical current that otherwise would be applied between the distal end 131 of the primary electrode 112 and the distal end 141 of the secondary electrode 122. Current-induced heating caused by the electrical current flowing across the current inrush regulator 101 causes the electrical current inrush regulator 101 to transition to the open position 103, thereby eliminating the temporary shunt. Thus, after an interval that reduces current-induced heating caused by the initial surge of current between the distal end 131 of the primary electrode 112 and the distal end 141 of the secondary electrode 122, a full degree of current—and resulting current-induced heating—flows between the distal end 131 of the primary electrode 112 and the distal end 141 of the secondary electrode 122 to facilitate application of current inducted heat at the electrically conductive target 105.

Figure 2:
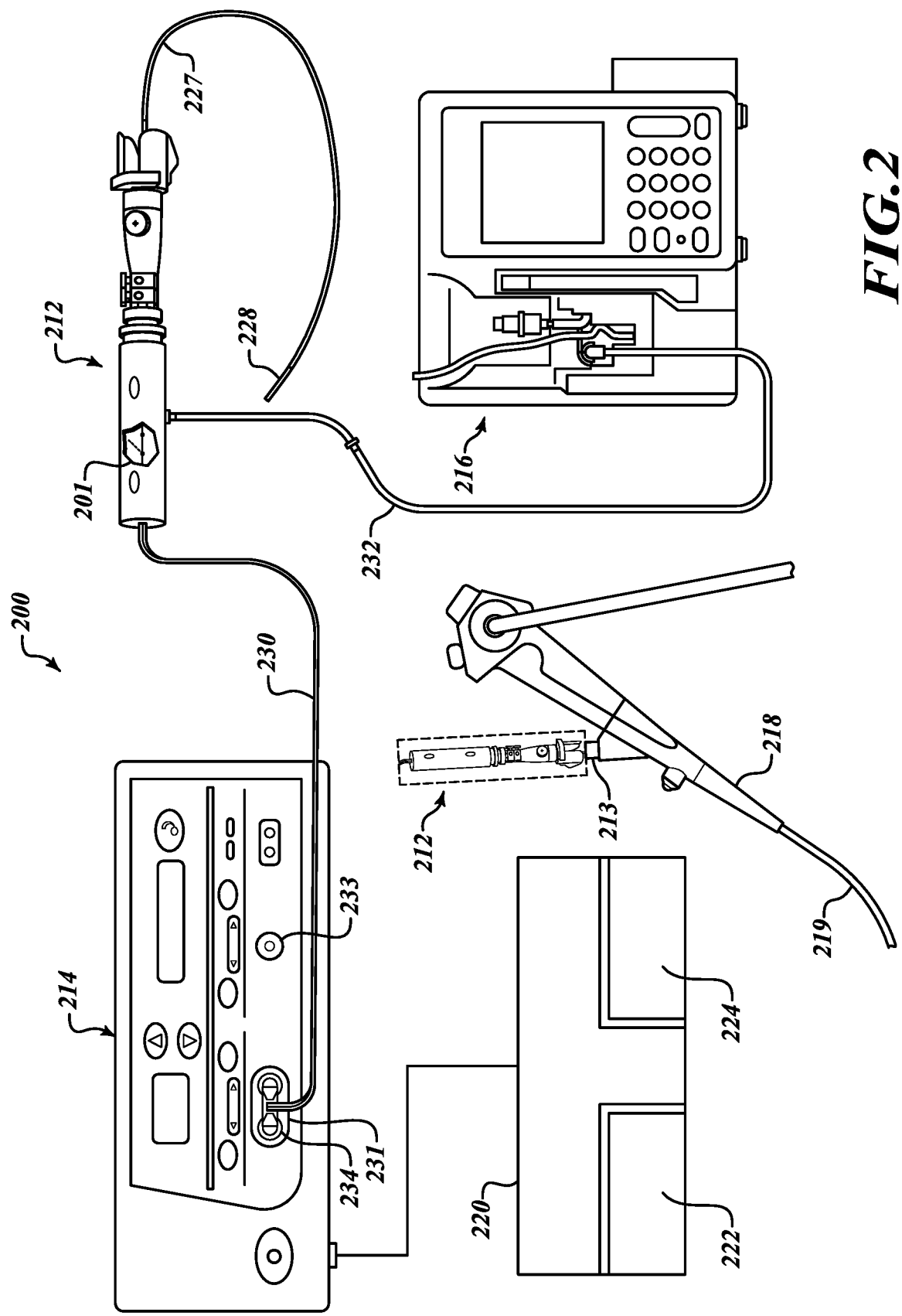
FIG. 2 is a block diagram in partial schematic form of an illustrative system for treating tissue.

Referring to FIG. 2, a system 200 is provided for treating tissue at an electrically conductive target in an anatomical region of a patient (not shown in FIG. 2). The system 200 may be a bipolar or monopolar radio frequency (RF) system, as desired, for treating tissue in a patient. Specifically, the system 200 may be employed for coagulation and/or ablation of soft tissue during percutaneous and/or endoscopic, including bronchoscopic, surgical procedures, such as, for example, partial and/or complete ablation of cancerous and/or noncancerous organ lesions. As will be further described, the tissue is treated by positioning one or more electrodes proximate the tissue to be treated and passing an electrical current through the tissue, which may be regarded as an electrically conductive target.

In some embodiments, the system 200 includes an applicator such as a positioning handle 212, an electrosurgical radio frequency (RF) generator operating as a switchable current source 214, an infusion pump 216, and a bronchoscope 218. The bronchoscope 218 may be configured to receive the positioning handle 212 at a port 213 to enable the positioning handle 212 to manipulate electrodes at the electrically conductive target via the bronchoscope 218.

The positioning handle 212 electrically communicates with the switchable current source 214 though an electrical conductor 230. In some embodiments, the electrical conductor 230 is connected to an outlet 231 when the system is operated in a bipolar mode. The electrical conductor 230 may be coupled with the outlet 231 using an electrical connector 234 configured to electrically engage the outlet 231. In some other embodiments, the system 200 can be operated in a monopolar mode when the electrical conductor 230 is connected to a secondary outlet 233 with an adapter (not shown in FIG. 2) as desired. The positioning handle 212 is further connected to the infusion pump 216 with a tube 232 that facilitates the flow of liquid, for example saline solution, from the pump 216 to the positioning handle 212.

The switchable current source 214 can be operated with the use of a foot-operated unit 220 electrically connected to the switchable current source 214. The foot-operated unit 220 includes a pedal 222 that instructs the switchable current source 214 to apply an electrical current to electrode(s) (described below) to cut and/or ablate tissue and a pedal 224 that instructs the generator 214 to apply a lower current to the electrode(s) to coagulate tissue.

In various embodiments the bronchoscope 218 includes an insertion tube 219 that permits insertion of a sheath 227 into a body. A distal end 228 of the sheath 219 is delivered to a location near the tissue to be treated. Positioning of the distal end 228 of the sheath 219 and the distal ends of the electrodes (not shown in FIG. 2) may be controlled by the positioning handle 212. In some embodiments, the current inrush regulator 201 may be incorporated within the positioning handle 212. As further described below with regard to FIG. 11, in other embodiments, a current inrush regulator also may be situated along the electrical conductor 230, within the electrical connector 234, or at another location where the current inrush regulator may be electrically coupled with the electrodes.

Figure 3:
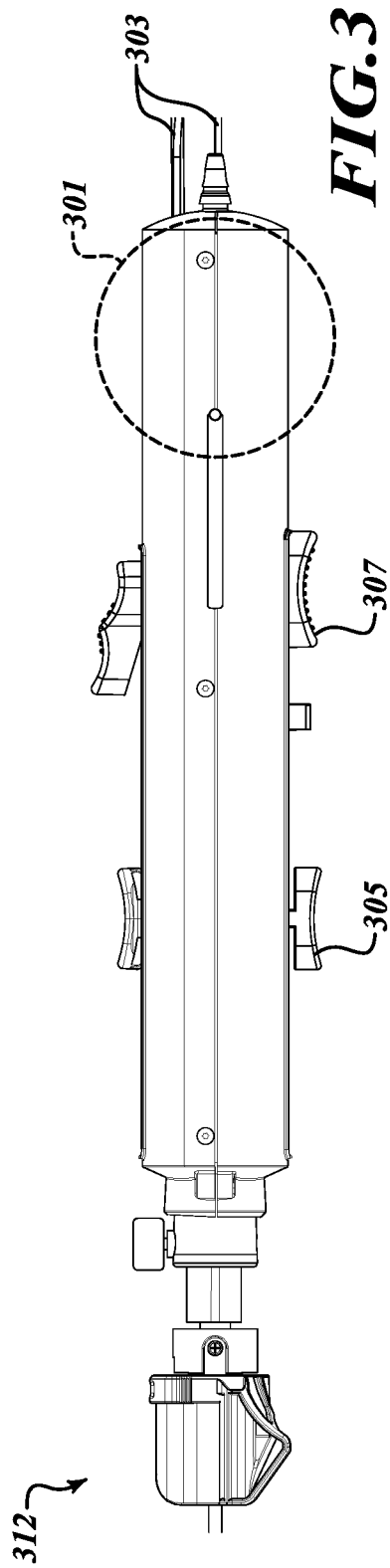
FIG. 3 is side view of an illustrative positioning handle.

Referring to FIG. 3, in another embodiment, a positioning handle 312 is similar to the positioning handle 212 of FIG. 2 and includes an embodiment of a current inrush regulator at a location 301. The positioning handle 312 receives leads 303, which may be part of an electrical conductor, such as the electrical conductor 230 of FIG. 2, which couples electrodes with a switchable current source (neither of which are shown in FIG. 3). The positioning handle 312 includes electrode actuators 305 and 307 that may be used to position distal ends of the electrodes, as described with reference to FIG. 1. In some embodiments, the actuators 305 and 307 manipulate sliders (not shown) mechanically coupled with the electrodes to slide the electrodes to desired locations. In some embodiments, a current inrush regulator may be disposed at the location 301 within the positioning handle 312 between the leads 303 and their electrical connections with proximal ends of the electrodes (not shown).

The current inrush regulator may take on a number of forms to temporarily shunt at least a portion of the electrical current between the electrodes. As described with reference to FIGS. 4-6, one form may include a fillable (and refillable) fluid chamber configured to temporarily form a shunt between the electrodes with electrically conductive fluid. FIGS. 7-10 illustrate other forms of current inrush regulators.

Figure 4:
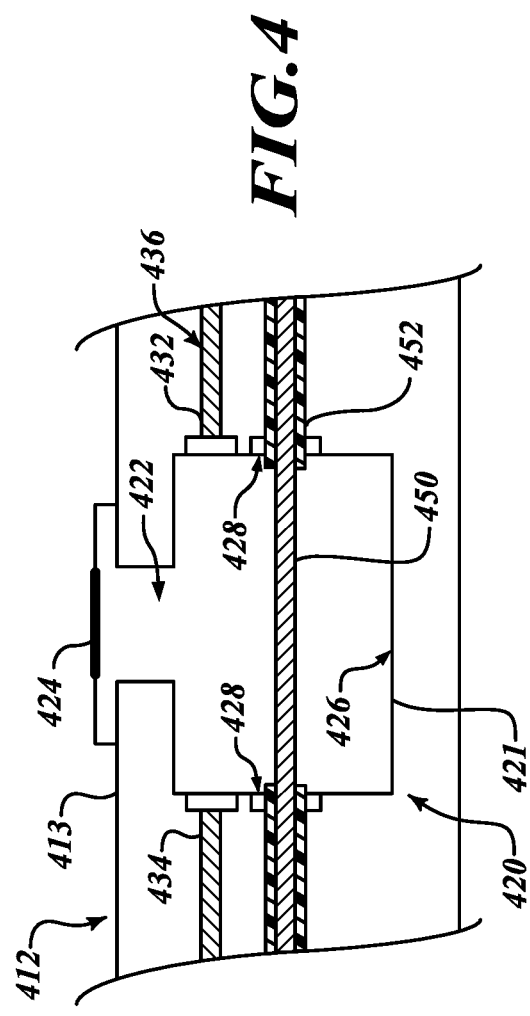
FIG. 4 is a cutaway view of a conductive fluid chamber disposed within the positioning handle of FIG. 3.

As described with reference to the following figures, embodiments of a current inrush regulator may include a circuit breaker, a fuse, or as shown in FIG. 4, a fluid chamber 420 that is disposed within a positioning handle 412 and that temporarily shunts current by heating a quantity of electrically conductive fluid (not shown in FIG. 4) to evaporation. It will be appreciated that the positioning handle 412 is similar to the positioning handle 212 and 312. The fluid chamber disposed within the positioning handle 412. In the embodiment of FIG. 4, the fluid chamber 420 includes a housing 421 that is secured to a surface 413 of the positioning handle 412. An opening 422 within the fluid chamber 420 is configured to receive the electrically conductive fluid. In some embodiments, a membrane 424 covers the opening 422 to contain the electrically conductive fluid therein, but is penetrable by an injector and permeable to steam (neither of which are shown in FIG. 4), as further described below with reference to FIGS. 5 and 6.

The fluid chamber 420 includes an electrically conductive inner chamber 426. The inner chamber 426 is electrically coupled with a first end 432 and a second end 434 of a first electrode 436, thereby forming an electrical connection between the first end 432 and the second end 434 of the first electrode 436 and with electrically conductive fluid that may be received within the inner chamber 426. The conductive chamber 420 also includes openings 428 through which a second electrode 450 may pass. Insulation 452 that may cover the second electrode 450 does not extend through the fluid chamber 420 so that the second electrode 450 is electrically exposed to electrically conductive fluid that may be received within the inner chamber 426. It should also be appreciated that, instead of the second electrode 450 extending through the inner chamber 426, the fluid chamber 420 may include a separate conductive element (not shown in FIG. 4) that is electrically insulated from the inner chamber 426 but electrically exposed to electrically conductive fluid that may be received within the inner chamber 426. In such embodiments, the separate conductive element is coupleable to the second electrode 450 outside the fluid chamber 420. In this embodiment, the second electrode would be coupled to the separate conductive element, much as the first end 432 and the second end 434 of the first electrode 436 are coupled to the inner chamber 426 as shown in FIG. 4.

Figure 5:
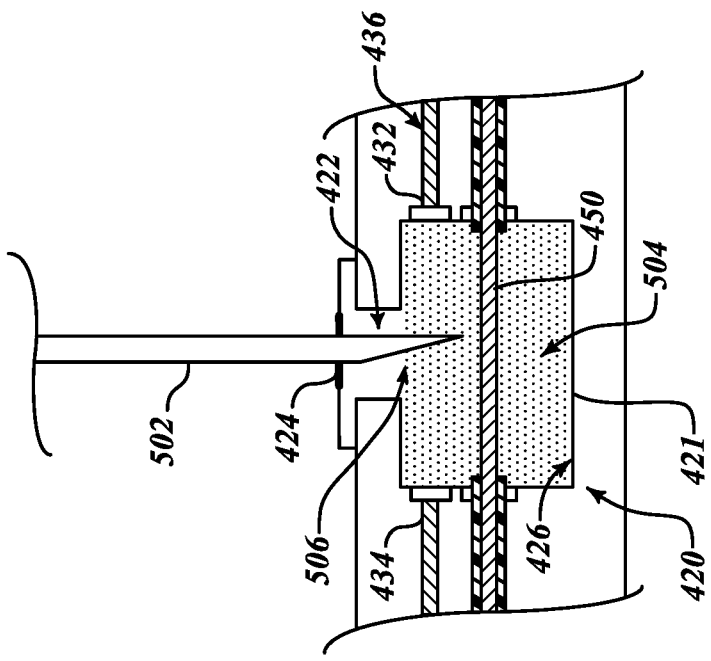
FIG. 5 is a cutaway view of the conductive fluid chamber of FIG. 4.

Referring to FIG. 5, in some embodiments the fluid chamber 420 of FIG. 4 is filled with the electrically conductive fluid 504 through the membrane 424 and the opening 422 that the membrane 424 covers. An injector 502, such as a hypodermic needle, may be filled with an electrically conductive fluid 504 which, without limitation, includes a saline solution. The injector 502 is then inserted through the membrane 424 to inject the electrically conductive fluid 504 into the inner chamber 426. A quantity of the electrically conductive fluid 504 is chosen to fill the inner chamber 426 to a desired fill level 506 to form an electrical connection between the inner chamber 426 and the second electrode 450 passing through the inner chamber 426.

Figure 6:
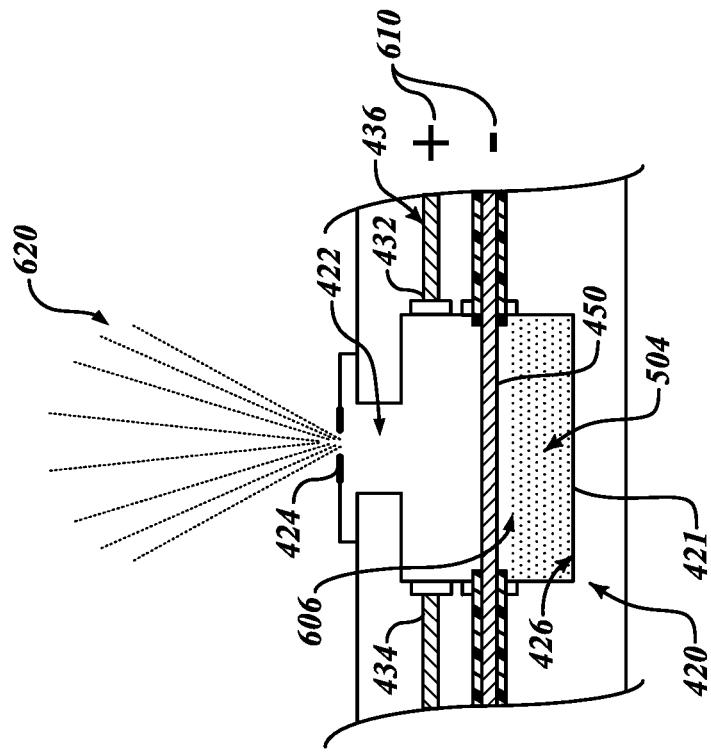
FIG. 6 is a cutaway view of the conductive fluid chamber of FIG. 5.

FIG. 6 is a cutaway view of the fluid chamber 420 of FIG. 5 after the inner chamber 426 has been filled with the electrically conductive fluid 504 and electrical current 610 has been applied to a first end 432 of the first electrode 436 and the second electrode 450. The electrically conductive fluid 504 electrically connects the first electrode 436 (via the inner chamber 426) and the second electrode 450. Electrical current 610 heats the electrically conductive fluid 504, thereby causing the electrically conductive fluid 504 to boil and generate steam 620, which passes out of the opening 422 in the fluid chamber 420 and through the membrane 424.

With continued application of the electric current 610 heating the electrically conductive fluid 504, the electrically conductive fluid 504 vaporizes until a fluid level 606 of the electrically conductive fluid 504 drops such that the electrically conductive fluid 504 no longer electrically connects the first electrode 436 (via the inner chamber 426) and the second electrode 450. In other words, when the electrical current 610 is applied between the first electrode 436 and the second electrode 450, the electrically conductive fluid 504 forms a shunt between the first electrode 436 and the second electrode 450 until the electrically conductive fluid 504 is sufficiently vaporized by current-induced heating to open the shunt.

It will be appreciated that different shapes and sizes of the fluid chamber 420 may be used as desired for particular applications to provide an inner chamber 426 that is configured to hold a quantity of the electrically conductive fluid 504 that will temporary divert a desired portion of the electrical current 610. To provide a non-limiting example, the inner fluid chamber 426 may be in the shape of a cylinder and a quantity of saline solution may be used as the electrically conductive fluid 504. As is known, the enthalpy of evaporation of water is 2256.5 kJ/kg at a typical room temperature and air pressure at sea level. Allowing, for example, five seconds for a system to react to a high current condition, then the power of evaporation of the fluid would be 451 W/kg. Using a density of water of 1 kg/m³ and an applied voltage of 200V (AC), Eqs. (1)-(4) may be solved for different sizes of the inner chamber 426 and the electrical current 610 applied to evaporate a provided quantity of saline solution:

Current=power/volts     (1)

Mass of saline=power/451 W/kg     (2)

Volume of saline=mass/density     (3)

Length of saline volume=volume/diameter     (4)

Using Eqs. (1)-(4), sample values may be calculated to indicate what parameters may be used to yield desired outcomes, as shown in Table (1) below:

TABLE 1

| Desired Power (W) | Current Limited to (A) | Diameter of Inner Chamber (mm) | Mass of Saline to Evaporate (kg) | Volume of Saline (m³) | Length of Inner Chamber (mm) |
|---|---|---|---|---|---|
| 5 | 0.025 | 0.5 | 0.01108 | 0.00001 | 22 |
| 10 | 0.050 | 0.5 | 0.02216 | 0.00002 | 44 |
| 15 | 0.075 | 1.0 | 0.03324 | 0.00003 | 33 |
| 20 | 0.100 | 1.0 | 0.04432 | 0.00004 | 44 |
| 25 | 0.125 | 1.0 | 0.05540 | 0.00006 | 55 |
| 30 | 0.150 | 1.0 | 0.06647 | 0.00007 | 66 |
| 35 | 0.175 | 2.0 | 0.07755 | 0.00008 | 39 |
| 40 | 0.200 | 2.0 | 0.08863 | 0.00009 | 44 |
| 45 | 0.225 | 2.0 | 0.09971 | 0.00010 | 50 |
| 50 | 0.250 | 2.0 | 0.11079 | 0.00011 | 55 |
| 55 | 0.275 | 2.0 | 0.12187 | 0.00012 | 61 |

These values are provided as a sample for purposes of illustration only and not of limitation. To that end, it will be appreciated that different shapes and sizes of the inner chamber may be used as desired for different applications, and different electrically conductive fluids may be used depending upon the application.

For example, if it were desirable to use a fluid chamber 420 having an inner chamber 426 of a cylindrical shape and of a particular length, the equations could be used to derive a diameter of the cylinder to achieve the desired parameters for temporarily diverting a portion of electrical current applied between electrodes. Alternatively, if a fluid chamber 420 having an inner chamber 426 of a different shape was used, whether that shape was spherical, cubic, rectangular, or of any other shape, equations for the volume of an inner chamber of that shape could be manipulated to determine the dimensions of that inner chamber 426 to achieve a desired result for temporarily diverting a portion of electrical current applied between electrodes. Further, if a different electrically conductive fluid was used instead of a saline solution, an enthalpy of evaporation for that different electrically conductive fluid could be used to derive the dimensions of the inner chamber 426 of the fluid chamber 420 to achieve a desired result for temporarily diverting a portion of electrical current applied between electrodes.

Figure 7:
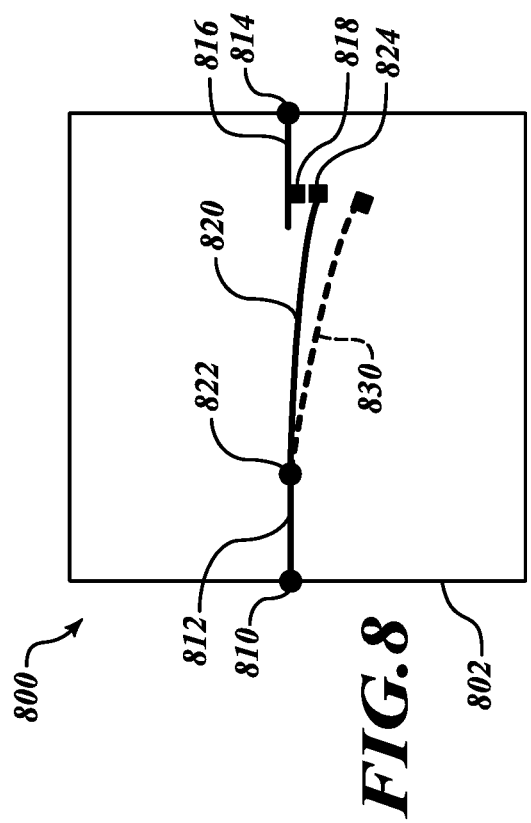
FIG. 7 is a cutaway view of a pre-filled conductive fluid chamber cartridge.

Referring to FIG. 7, in some embodiments a pre-filled conductive fluid chamber cartridge 700 may be used as a current inrush regulator. The chamber cartridge 700 includes a housing 702 configured to contain a quantity of electrically conductive fluid 704. The housing 702 may be filled through an opening 724 in the housing 702. After the housing 702 is filled with the electrically conductive fluid 704, the opening 724 is plugged with a membrane 726. The membrane 726 is configured to contain the electrically conductive fluid 704 in a liquid state but to permit a vaporized form of the electrically conductive fluid 704 to permeate the membrane 726 when the electrically conductive fluid 704 is vaporized. When the chamber cartridge 700 is coupled between first and second electrodes (not shown in FIG. 7), the chamber cartridge 700 thus forms a shunt between the first and second electrodes.

The pre-filled conductive fluid chamber cartridge 700 also includes a first terminal 710 coupled with a first internal contact 712 and a second terminal 714 coupled with a second internal contact 716. The first terminal 710 is configured to be electrically engaged by a contact coupled with one of the first electrode and the second electrode used to apply a treatment, as previously described with reference to FIGS. 1 and 4-6. The second terminal 714 is configured to be electrically engaged by a contact coupled with the other of the first electrode and the second electrode. The first internal contact 712 and the second internal contact 716 engage the electrically conductive fluid 704 to form a shunt between the first internal contact 712 and the second internal contact 716. When current is applied between the first and second electrode and, thus, through the first internal terminal 712 and the second internal terminal 716, the electrically conductive fluid 704 shunts the electrical current until current induced heating causes the electrically conductive fluid to vaporize and open the shunt circuit, as previously described with reference to FIG. 6.

Figure 8:
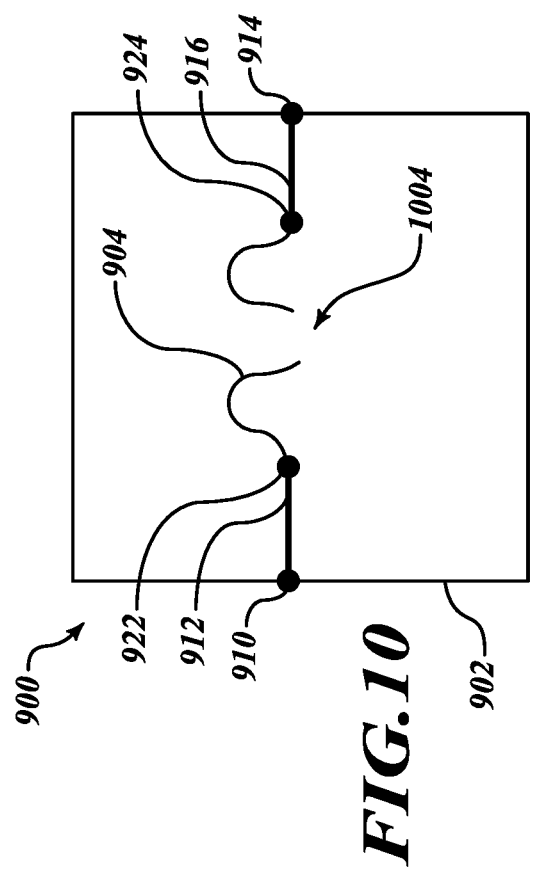
FIG. 8 is a cutaway view of a circuit breaker.

Referring to FIG. 8, in some embodiments a circuit breaker 800 may be used as a current inrush regulator. The circuit breaker 800 may be received within a housing 802. The circuit breaker 800 includes a first terminal 810 coupled with a first internal connector 812 and a second terminal 814 coupled with a second internal connector 816. The first terminal 810 is configured to be electrically engaged by a contact coupled with one of the first electrode and the second electrode used to apply a treatment, as previously described with reference to FIGS. 1 and 4-6 (and not shown in FIG. 8). The second terminal 814 is configured to be electrically engaged by a contact coupled with the other of the first electrode and the second electrode. The first internal connector 812 is fixably coupled at a first electrical joint 822 with a trip member 820. An opposite end of the trip member 820 may support a contact point 824 configured to engage a fixed contact point 818 disposed on an end of the second internal connector 816. When the circuit breaker 800 is coupled between first and second electrodes, the circuit breaker 800 thus forms a shunt between the first and second electrodes.

In some embodiments, the trip member 820 may include a bimetal strip composed of metals having different coefficients of expansion such that the two metals expand at different rates when heated. As a result, upon being heated, one side of the trip member 820 would bend toward the side comprised of the metal having the lower coefficient of expansion, as depicted by dashed line 830. The bending of the trip member 820 would move the contact point 824 away from the fixed contact point 818, causing the circuit breaker 800 to open.

Thus, starting with the trip member 820 in an initial, undeformed state, the contact point 824 on the trip member 820 engages the fixed contact point 818 to shunt at least a portion of the electrical current applied between the first electrode and the second electrode. However, as electrical current continues to flow through the trip member 820, current induced heating causes the trip member 820 to deform, thereby moving the contact point 824 away from the fixed contact point 818 to open the shunt circuit.

Figure 9:
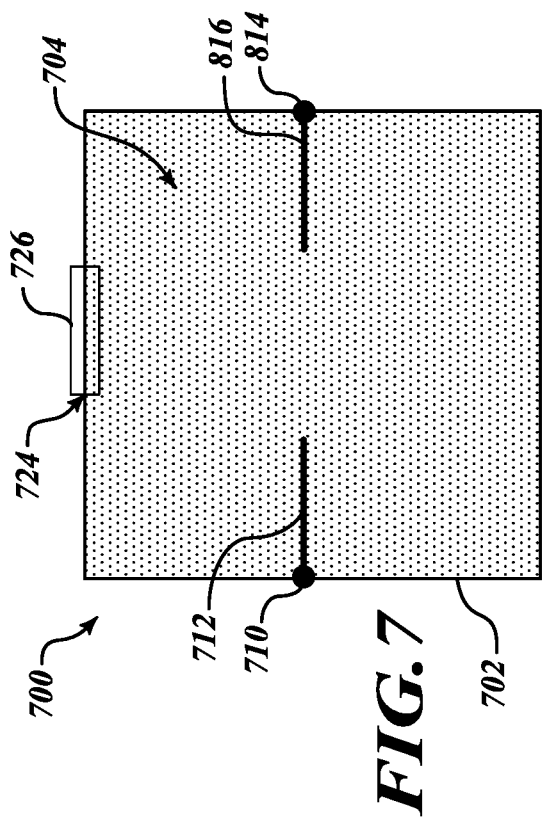
FIG. 9 is a cutaway view of a fuse before application electrical of current.

Referring to FIG. 9, a fuse 900 may be used as a current inrush regulator. The fuse 900 may be received within a housing 902. The fuse 900 includes a first terminal 910 coupled with a first internal connector 912 and a second terminal 914 coupled with a second internal connector 916. The first terminal 910 is configured to be electrically engaged by a contact coupled with one of the first electrode and the second electrode used to apply a treatment, as previously described with reference to FIGS. 1 and 4-6 (not shown in FIG. 9). The second terminal 914 is configured to be electrically engaged by a contact coupled with the other of the first electrode and the second electrode. The first internal connector 912 is fixably coupled at a first electrical joint 922 with an end of a fuse element 904. An opposite end of the fuse element 904 is coupled at a second electrical joint 924 with the second internal connector 916. The fuse element 904 may be comprised of a thin wire comprised of a material such as aluminum, zinc, or another metal as desired for a particular application. The fuse element 904 is configured to melt when current induced heating causes the fuse element 904 to exceed a threshold temperature. When the fuse 900 is coupled between first and second electrodes, the fuse element 904 thus forms a shunt between the first and second electrodes.

Figure 10:
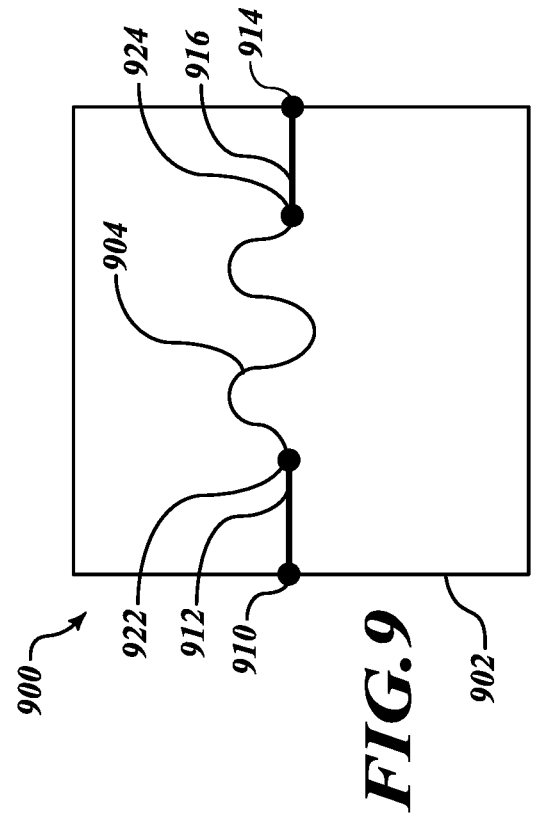
FIG. 10 is a cutaway view of a fuse after the application of electrical current.

Referring to FIG. 10, current induced heating of the fuse element 904 has caused the fuse element 904 to melt, resulting in a break 1004 in the fuse element 904 that opens the shunt circuit. Thus, when the fuse 900 is coupled between the first and second electrodes, the fuse 900 provides a temporary shunt between the first and second electrodes to at least partially divert electrical current applied between the first and second electrodes. However, once current induced heating caused by the diverted electrical current causes the break 1004 in the fuse element 904, the shunt circuit opens.

Figure 11:
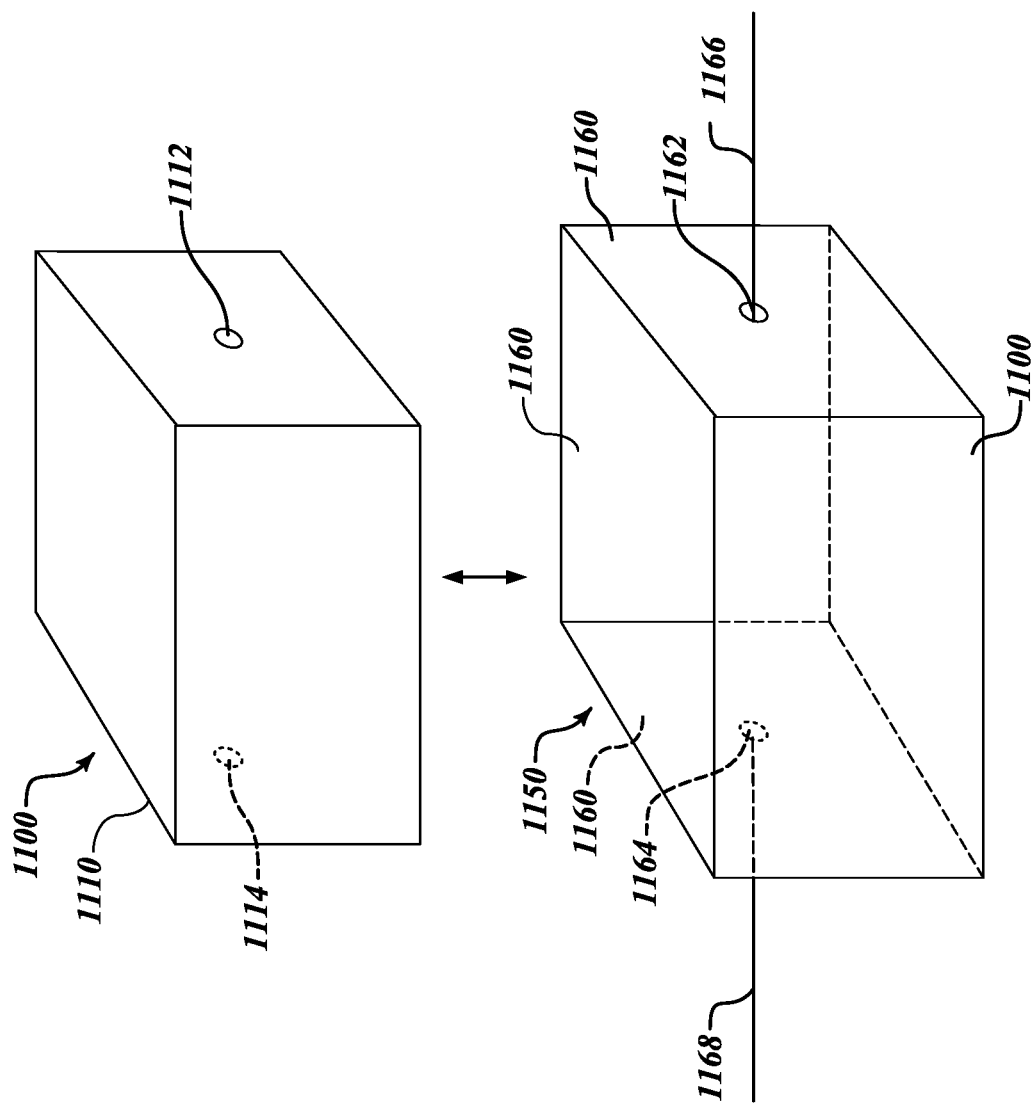
FIG. 11 is a perspective view of an illustrative replaceable current inrush regulator and a receptacle configured to receive the replaceable current inrush regulator.

Referring to FIG. 11, in some embodiments the current inrush regulator may include a replaceable current inrush regulator 1100. In such embodiments, a receptacle 1150 is configured to receive the replaceable current inrush regulator 1100. The replaceable current inrush regulator 1100 may include any form of current inrush regulator, such as a refillable conductive fluid chamber, a pre-filled conductive fluid chamber, a circuit breaker, a fuse, or another form of current inrush regulator. The replaceable current inrush regulator 1100 includes a housing 1110 supporting a first terminal 1112 and a second terminal 1114 configured to be engaged by a first contact 1162 and a second contact 1164, respectively, within the receptacle 1150. In some embodiments, the housing 1110 is sized to closely fit within sides 1160 of the receptacle 1150 to permit the replaceable current inrush regulator to be received therein while forcibly causing the first terminal 1112 and the second terminal 1114 to engage the first contact 1162 and the second contact 1164, respectively. Once the replaceable current inrush regulator 1100 is inserted within the receptacle 1150, the replaceable current inrush regulator forms a temporary shunt between the first and second electrodes, as previously described with reference to FIGS. 1 and 4-6.

Figure 12:
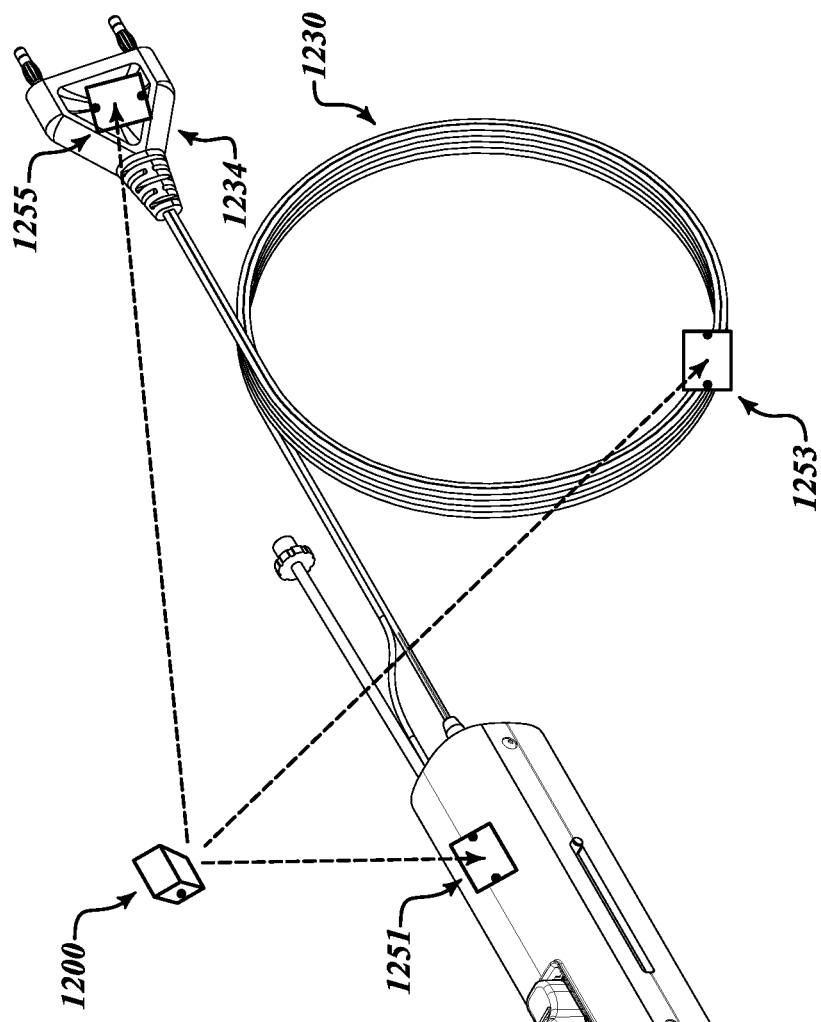
FIG. 12 is a perspective view of an illustrative positioning handle, associated electrical conductor, and an electrical connector of FIG. 2.

Referring to FIG. 12, a positioning handle 1212, an associated electrical conductor 1230, and an electrical connector 1234, are similar to comparable components 212, 230, and 234, respectively, of FIG. 2, and are equipped with receptacles 1251, 1253, and 1255, are configured to receive a current inrush regulator 1200. It will be appreciated that multiple current inrush regulators need not be used, but that the receptacles 1251, 1253, and 1255 represent positions that may receive the current inrush regulator 1200. In some embodiments, only one of the receptacles 1251, 1253, and 1255 may be provided. In some other embodiments, two or three of the receptacles 1251, 1252, and 1253 may be provided, as desired for particular applications. The current inrush regulator received may include a refillable fluid chamber, as described with reference to FIGS. 4-6 or a circuit breaker described with reference to FIG. 8. The current inrush regulator may also include a replaceable current inrush regulator, such as a conductive fluid chamber as described with reference to FIG. 7 or a fuse as described with reference to FIGS. 9 and 10.

It will be understood from previous description of the various embodiments that the current inrush regulator may be positioned at any physically convenient location between the switchable current source 214 (FIG. 2) and distal ends 131 of the first electrode 112 and the distal end 141 of the second electrode 122 (FIG. 1) as long as the current inrush regulator 1200 may be coupled in parallel with the first electrode 112 and the second electrode 122. Accordingly, the current inrush regulator 1200 may be disposed within the positioning handle 1212, either fixedly as described with reference to FIGS. 3-6 or replaceably within the receptacle 1251. The current inrush regulator 1200 also may be disposed at any point along the electrical conductor 1230, either fixably or replaceably, such as within the receptacle 1253. The current inrush regulator 1200 also may be disposed within electrical connector 1234, either fixably or replaceably, such as within the receptacle 1255.

Figure 13:
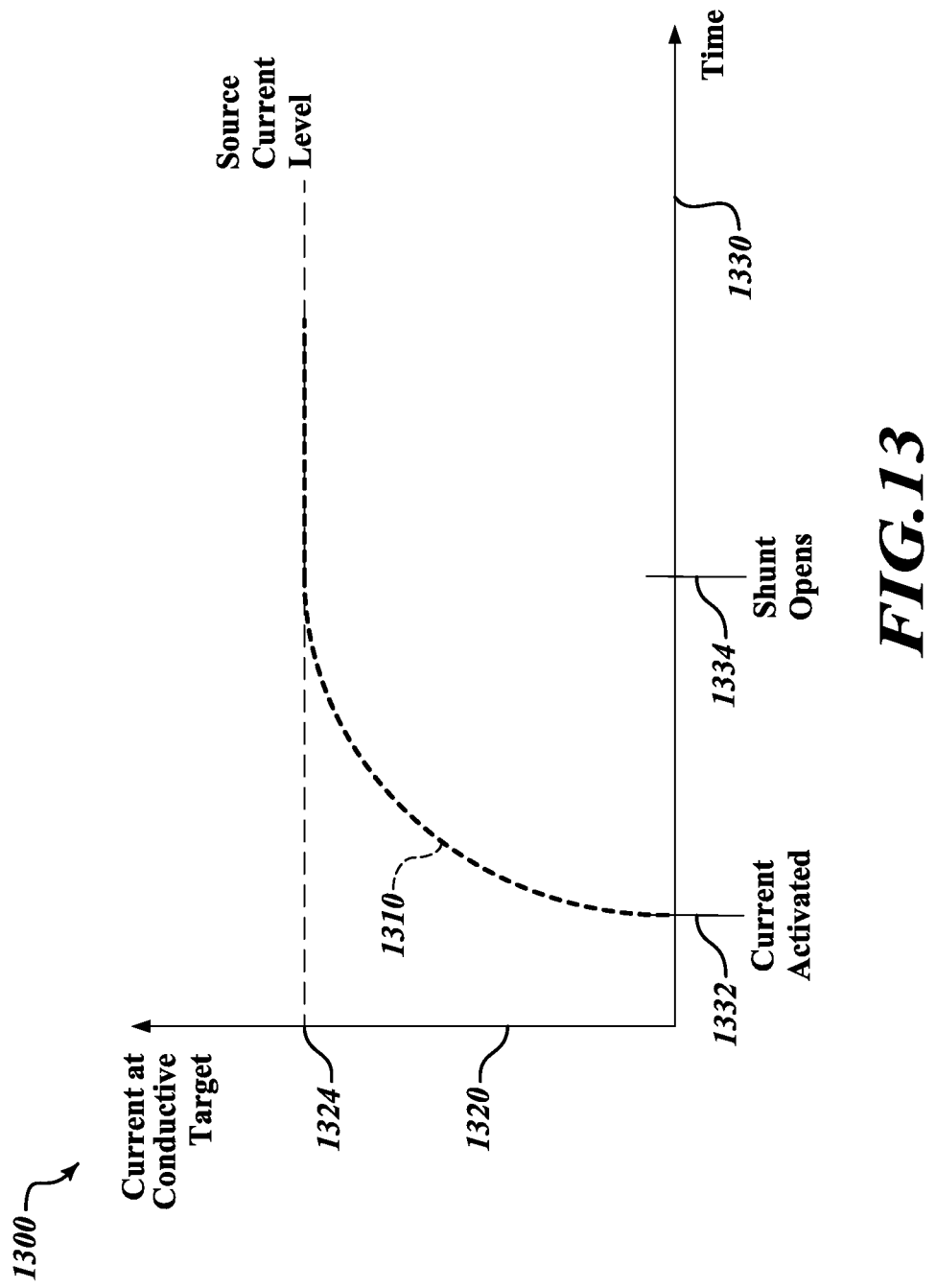
FIG. 13 is a graph representing temporary reduction of current at the conductive target over time resulting from use of an embodiment of the current inrush regulator.

Referring to FIG. 13, a graph 1300 represents temporary reduction of electrical current at the conductive target over time resulting from use of a current inrush regulator. The graph 1300 plots electrical current at the conductive target on a dependent axis 1320 versus time plotted on an independent axis 1330. A source current level 1324 is the maximum current generated by the switchable current source 214 (FIG. 2). At a point 1332, the switchable current source 214 is activated. Instead of the electrical current at the conductive target immediately reaching the source current level 1324, various embodiments of the current inrush regulator temporarily shunt at least a portion of the electrical current, as previously described. However, as plot 1310 shows, after an interval, an amount of electrical current diverted by current inrush regulator diminishes, such as when the electrically conductive fluid vaporizes, a fuse element melts, etc., and the shunt opens at a point 1134. Thus, the electrical current at the conductive target does not immediately reach the source current level 1324.

Referring, FIG. 14, an illustrative method 1400 of using a current inrush regulator is provided. The method 1400 starts at a block 1405. At a block 1410, electrical current is shunted between first and second electrodes through a temporary shunt circuit. The first and second electrodes each have a distal end and are configured to conduct electrical current generated by a switchable current source between the distal ends and through an electrically conductive target, as previously described with reference to FIG. 1. The temporary shunt circuit may include a fixed current inrush regulator, such as the conductive fluid chamber described with reference to FIGS. 4-6 or a circuit breaker described with reference to FIG. 8. When the temporary shunt circuit includes a conductive fluid chamber, shunting the electrical current between the first and second electrodes may include filling the conductive fluid chamber with electrically conductive fluid, such as saline solution, or by resetting a circuit breaker. The temporary shunt circuit also may include a replaceable current inrush regulator, such as a pre-filled conductive fluid chamber as described with reference to FIG. 7 or a fuse as described with reference to FIGS. 9 and 10. When the temporary shunt circuit includes a replaceable current inrush regulator, shunting the electrical current between the first and second electrodes may include replacing a pre-filled conductive fluid chamber or a fuse.

At a block 1420, the switchable current source is activated to apply the electrical current between the first and second electrodes, where the electrical current applied through the electrically conductive target by the first and second electrodes is temporarily reduced by a portion of the electrical current passing through the temporary shunt circuit. As described with reference to FIGS. 1 and 4-10, a current inrush regulator shunts current between the electrodes to reduce the electrical current applied through distal ends of the electrodes.

At a block 1430, the electrical current continues to be applied from the switchable current source while heat caused by the electrical current flowing through the temporary shunt circuit causes the temporary shunt circuit to open. Once the temporary shunt circuit presented by the current inrush regulator opens, such as when the electrically conductive fluid boils away to break the connection between the electrodes, when the circuit breaker opens, or when the fuse element melts, the full electrical current generated by the switchable current source is applied by the distal ends of the electrodes through the electrically conductive target. The method ends at a block 1435

It will be appreciated that the detailed description set forth above is merely illustrative in nature and variations that do not depart from the gist and/or spirit of the claimed subject matter are intended to be within the scope of the claims. Such variations are not to be regarded as a departure from the spirit and scope of the claimed subject matter.

What is claimed is:

1. An apparatus comprising:
   a first electrode including a distal end configured to deliver an electrical current to an electrically conductive target and a proximal end;
   a second electrode including a distal end configured to receive the electrical current conducted through the electrically conductive target from the first electrode;
   a switchable current source electrically coupled between the proximal end of the first electrode and a proximal end of the second electrode; and
   a current inrush regulator including a fluid chamber including a refillable housing adapted to receive an electrically conductive fluid and temporarily electrically couple in parallel the switchable current source to the proximal end of the first electrode and the proximal end of the second electrode and configured to temporarily shunt a portion of the electrical current generated by the switchable current source to temporarily reduce the electrical current passing between the distal end of the first electrode and the distal end of the second electrode through the electrically conductive target, wherein the current inrush regulator transitions to an open position to disable the temporary shunt after evaporation of at least a portion of the electrically conductive fluid.

2. The apparatus of claim 1, wherein the fluid chamber includes:
   the housing having an electrically conductive inner chamber;
   a first electrode coupling configured to electrically connect the first electrode to the electrically conductive inner chamber; and
   a second electrode coupling electrically insulated from the electrically conductive inner chamber and configured to make an electrical connection between the second electrode and an interior of the electrically conductive inner chamber to close a shunt circuit between the first electrode and the second electrode when the electrically conductive fluid is present in the electrically conductive inner chamber.

3. The apparatus of claim 2, wherein the housing defines therein at least one opening configured to at least one of:
   receive a quantity of the electrically conductive fluid into the electrically conductive inner chamber; and
   vent steam generated by evaporation of at least a portion of the electrically conductive fluid caused by heating of the electrically conductive fluid by the electrical current.

4. The apparatus of claim 3, wherein the housing further includes a pierceable membrane sealingly disposed over the at least one opening and configured to pierceably receive therethrough an injector configured to insert the electrically conductive fluid.

5. The apparatus of claim 2, wherein the electrically conductive fluid includes a saline solution.

6. The apparatus of claim 2, wherein the fluid chamber is fixably coupleable with the first electrode and the second electrode, and wherein the electrically conductive inner chamber is further configured to be refillable with the electrically conductive fluid.

7. The apparatus of claim 2, wherein the fluid chamber is removably coupleable with the first electrode and the second electrode to permit replacement of the electrically conductive inner chamber.

8. The apparatus of claim 1, further comprising:
   a positioning handle configured to manipulate positions of the first and second electrodes;
   an electrical connector electrically coupleable with a plurality of output ports of the switchable current source; and
   an electrical conductor configured to electrically connect the first and second electrodes to the electrical connector; and
   wherein the current inrush regulator is disposed in one of the positioning handle, the electrical connector, and the electrical conductor.

9. A system for treating tissue at an electrically conductive target, the system comprising:
   a switchable current source configured to selectively provide electrical power between a first pole and a second pole;
   a bronchoscope configured to be inserted into a body to convey a sheath towards a vicinity of an electrically conductive target, the sheath containing a primary electrode electrically coupleable to the first pole and a secondary electrode electrically coupleable to the second pole;
   a positioning handle configured to position distal ends of the primary electrode and the secondary electrode relative to the electrically conductive target;
   an electrical conductor configured to electrically connect the primary electrode to the first pole of the switchable current source and to connect the secondary electrode to the second pole of the switchable current source; and
   a current inrush regulator electrically coupled in parallel with proximal ends of the primary electrode and the secondary electrode to create a temporary shunt that diverts at least a portion of an electrical current generated by the switchable current source to temporarily reduce the electrical current passing between the distal ends of the primary and secondary electrodes through the electrically conductive target, wherein the current inrush regulator includes a refillable conductive fluid chamber adapted to hold an electrically conductive fluid to temporarily conduct current between the primary electrode and the secondary electrode through the fluid chamber and transition to an open position to disable the temporary shunt after evaporation of at least a portion of the electrically conductive fluid.

10. The system of claim 9, wherein the fluid chamber includes:
a housing having an electrically conductive inner chamber and configured to receive the electrically conductive fluid;
a first electrode coupling configured to electrically connect the primary electrode to the electrically conductive inner chamber; and
a second electrode coupling electrically insulated from the electrically conductive inner chamber and configured to electrically connect the secondary electrode to an interior of the electrically conductive inner chamber to close a shunt circuit between the primary electrode and the secondary electrode when the electrically conductive fluid is present in the electrically conductive inner chamber, the electrically conductive fluid being heatable by the electrical current upon activation of the controllable electrical power source until evaporation of at least a portion of the electrically conductive fluid opens the shunt circuit between the primary electrode and the secondary electrode.

11. The system of claim 10, wherein the housing defines therein at least one opening configured to at least one of:
receive a quantity of the electrically conductive fluid into the electrically conductive inner chamber; and
vent steam generated by evaporation of at least a portion of the electrically conductive fluid caused by heating of the electrically conductive fluid by the electrical current.

12. The system of claim 10, wherein the electrically conductive inner chamber is one of:
fixably coupleable with the primary electrode and the secondary electrode, and wherein the electrically conductive inner chamber is configured to be refillable with the electrically conductive fluid; and
removably coupleable with the primary electrode and the secondary electrode to permit replacement of the electrically conductive inner chamber.

13. A method comprising:
shunting electrical current between first and second electrodes through a temporary shunt circuit coupled in parallel with a switchable current source, each of the first and second electrodes having a distal end and being configured to conduct electrical current generated by the switchable current source between the distal ends and through an electrically conductive target;
filling a refillable housing disposed in the temporary shunt circuit with electrically conductive fluid prior to activating the switchable current source, wherein the electrically conductive fluid electrically couples the first and second electrodes;
activating the switchable current source to apply the electrical current between the first and second electrodes, wherein a portion of the electrical current is redirected through the temporary shunt circuit resulting in the electrical current applied through the electrically conductive target by the first and second electrodes being reduced by the portion of the electrical current passing through the temporary shunt circuit; and
continuing to apply the electrical current from the switchable current source while heat caused by the electrical current flowing through the temporary shunt circuit causes the temporary shunt circuit to open due to evaporation of the electrically conductive fluid, wherein a level of the electrical current flowing through the distal ends of the first and second electrodes and the electrically conductive target is no longer reduced by the portion when the temporary shunt circuit opens.

* * * * *